US006902532B2

(12) United States Patent
Lomask

(10) Patent No.: US 6,902,532 B2
(45) Date of Patent: Jun. 7, 2005

(54) REDUCED-NOISE PLETHYSMOGRAPH

(75) Inventor: Joseph Lomask, Wilmington, NC (US)

(73) Assignee: Buxco Electronics, Inc., Sharon, CT (US)

( * ) Notice: Subject to any disclaimer, the term of this patent is extended or adjusted under 35 U.S.C. 154(b) by 82 days.

(21) Appl. No.: 10/461,008

(22) Filed: Jun. 12, 2003

(65) Prior Publication Data

US 2004/0254489 A1 Dec. 16, 2004

(51) Int. Cl.[7] .......................... A61B 5/08; A61M 11/00; G01N 17/00

(52) U.S. Cl. .................. 600/529; 128/200.14; 73/865.6

(58) Field of Search ................................ 600/529–543; 128/200.14, 204.18; 119/420; 73/1.57, 865.6

(56) References Cited

U.S. PATENT DOCUMENTS 4,479,493 A * 10/1984 Bung et al. ............ 128/204.18
4,520,808 A * 6/1985 LaBauve ............... 128/200.14
H000145 H * 10/1986 James ........................ 600/529
4,622,852 A * 11/1986 James et al. ............... 73/865.6
4,841,982 A * 6/1989 Nikiforov et al. .......... 600/529
4,947,339 A * 8/1990 Czekajewski et al. ........ 702/24
4,972,842 A 11/1990 Korten et al.
5,305,763 A * 4/1994 Ganshorn ................... 600/543
5,379,777 A * 1/1995 Lomask ...................... 600/529
5,513,648 A 5/1996 Jackson
5,620,005 A * 4/1997 Ganshorn ................... 600/529

* cited by examiner

*Primary Examiner*—Robert Nasser
*Assistant Examiner*—Navin Natnithithadha
(74) *Attorney, Agent, or Firm*—MacCord Mason PLLC

(57) ABSTRACT

The accuracy of measurements of changes in air volumes within a plethysmograph is improved by addition of a manifold to provide a common source of exterior air to the plethysmograph test and reference chamber. The preferred plethysmograph includes test and reference chambers divided by a common separator wall, pneumotachs in communication with the chambers, and a differential pressure transducer having a first inlet in communication with the test chamber and a second inlet in communication with the reference chamber. The manifold includes an exterior air inlet and a passageway extending between the two pneumotachs and the air inlet. The passageway may be in the form of separate tubes or conduits, or a common housing covering the pneumotachs. Preferably, the distances from the exterior air inlets to the two pneumotachs are approximately the same.

18 Claims, 5 Drawing Sheets

70 78 74 72 80 60 30 20 80 38 62 48 14 44 18 16 46 12 10 64 22 24 64

78
70
74
72
60
80
30
20
80
38
62
48
14
44
18
16
46
12
10
64
22
24
64

78
70
72
74
32
60
40
80
80
30
38
36
42
34
20
14
18
16
62
12
26
22
24
64

58
56
54
50
50
44
16
14
18
12

148
146
154
142
140
104
152
106
134
108
132
102
130
100
110

152
148
146
152
142
140
100
154
106
150
144
110
108
104
102
112

162
160
166
164
170
168

166
160
162
170
164

(A)
(B)

REDUCED-NOISE PLETHYSMOGRAPH

BACKGROUND OF THE INVENTION (1) Field of the Invention

The present invention relates to plethysmographs used for measuring changes in air volume, such as in non-invasive pulmonary testing of small animals, and in particular to plethysmographs in which transducer noise is substantially reduced, improving the accuracy of test data.

(2) Description of the Prior Art

Plethysmographs are used in research to collect data relating to changes in air pressure within a test chamber. An example of such data is pulmonary data from small animals, such as mice. Most plethysmographs are comprised of a test chamber to enclose the test subject, a reference chamber, and a differential pressure transducer connected to the two chambers, e.g., via tubing extending from a port in each chamber to the transducer. Both chambers are in communication with the ambient air, i.e., the air within the room where the tests are being conducted, through restricted airflow openings, or pneumotachs.

As changes to the air volume within the test chamber occur, pressure variations are recorded by the transducer, which normally displays the recorded data in numerical form or as a graph. Air pressure within the test chamber can also vary due to changes in the pressure of air entering the test chamber through the pneumotachs. This non-chamber originated air pressure variation, known as background noise or simply noise, can adversely affect the accuracy of the recorded data, since the transducer also measures the noise.

Plethysmographs are commonly used to measure the pulmonary activities of small animals, such as mice, that are completely or substantially enclosed within the test chamber. As the test animal inhales or exhales, the changes in air volume results in pressure variations that are recorded by the transducer, which normally displays the recorded data in numerical form or as a graph.

The purpose of the reference chamber is to partially reduce the noise affect. A second tube extends from a reference chamber outlet to the transducer. The transducer simultaneously measures variations in air pressures within the two chambers, and subtracts the reference chamber measurements from the animal chamber measurements. As a result, the net pressure variations are essentially attributable to the respiration patterns of the test animal. Preferably, the test and reference chamber pneumotachs are close to each other to minimize variations in exterior air patterns.

A representative plethysmograph of the type used to measure small animal pulmonary responses is shown and described in commonly assigned U.S. Pat. No. 5,379,777 to Lomask, the entire disclosure of the patent being incorporated herein by reference.

While a reference chamber partially addresses the problem of noise in transducer-measured plethysmographs, variations due to air pressure differences still remain. Thus, a level of noise still occurs, which can adversely affect test results, particularly in sensitive measurement. Thus, there is still a need for an apparatus and method for lessening the effect of ambient air changes in plethysmographs used for animal pulmonary measurements, as well as other testing of air volume changes within a test chamber.

SUMMARY OF THE INVENTION

The present invention is directed to an improved plethysmograph and method for measuring pressure changes within a test chamber, while minimizing the effect of noise created by ambient air variations. Generally, the improved plethysmograph is comprised of a test chamber to enclose the test subject, e.g., a small animal, a reference chamber, a transducer, and an air manifold to provide air to the two chambers.

The test chamber includes a housing to enclose the test subject. Preferably, the housing is formed of a cylindrical sidewall, an upper and a bottom wall. An airflow opening is positioned in the housing wall to permit air to flow to and from the test chamber due to pressure changes. The airflow opening may be a pneumotach or pneumotachograph, which is basically a restricted airflow opening that may include a screen covering the opening to create a pressure drop.

The test chamber may also include a bias-air outlet connected to a vacuum source to draw air through the test chamber to reduce heat and humidity within the chamber and prevent the test animal from rebreathing air. If a test gas or aerosol is to be inserted into the chamber, the test chamber may also include an aerosol inlet or manifold having an inlet connectible to a gas or aerosol source, and an outlet within the test chamber. When the plethysmograph is used in testing small animals, the test chamber may also include a perforated floor spaced above the bottom wall to separate the animal from feces and urine.

The reference chamber includes an airflow opening, which may be a pneumotach, in the housing wall to permit air to flow to and from the reference chamber due to pressure changes. The reference chamber is preferable proximate to the test chamber to minimize variations in external air conditions between the airflow openings of the two chambers. For example, the two chambers may be separated by a common wall.

The two chambers also include outlets or ports for connecting a differential pressure transducer to the two chambers. For example, a block may be attached to the exterior wall of the plethysmograph with ports extending through the wall into the two chambers. Tubes may then extend from the ports to the transducer. The transducer is in turn connected to a recorder, usually through an amplifier, to record changes in air pressure, indicating changes in air volume. Simultaneous measurement of air changes within the reference chamber permits changes in exterior air pressure to be partially subtracted from the measured values. As a result, the recorded measurements largely reflect actual pressure changes created by the test subject within the test chamber.

In accordance with the present invention, noise affecting accurate readings of pressure changes within the test chamber is further reduced by the addition of a manifold to the plethysmograph. As used herein, the term "manifold" is used to define an air passageway or conduit adapted to communicate with the airflow openings into the test and reference chambers, and an exterior airflow opening from the exterior of the manifold into the passageway. The passageway can be in the form of a housing that encloses the inlets, tubes that separately connect to the chamber openings and to a common exterior opening, or conduits drilled within a solid block of material to connect the chamber airflow openings and the exterior airflow opening. Preferably, the distances from the exterior airflow opening to the test and reference chamber airflow openings are approximately the same distance, so that air entering the exterior airflow opening will have about the same distance to travel to reach the test and reference chamber airflow openings.

It has been found that addition of this manifold further minimizes the effect of changes in exterior air, since the air enters both chambers from a common opening. Thus, as opposed to prior art devices in which exterior air entered directly into the chambers through separate openings, any changes in air entering the manifold opening will be equally experienced by both chambers at approximately the same time, especially if the exterior opening is approximately equidistant from the respective chamber openings. As a result, subtraction of reference chamber pressures from test chamber pressures provides essentially a noise-free measurement of pressure changes within the test chamber that is attributable to the test subject.

The specific construction of the manifold, which may be installed at the time the plethysmograph is manufactured, or later as an aftermarket accessory, will vary dependent upon the configuration of the specific plethysmograph, and in particular the location of the chamber openings or pneumotachs. The exact construction will also depend upon whether a common housing or separate tubes or conduits are preferred for the particular application. In any event, however, the accuracy of pressure readings by the transducer is significantly improved, particularly in highly sensitive measurements, by addition of the manifold described herein.

DETAILED DESCRIPTION OF THE INVENTION

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

Figure 1:
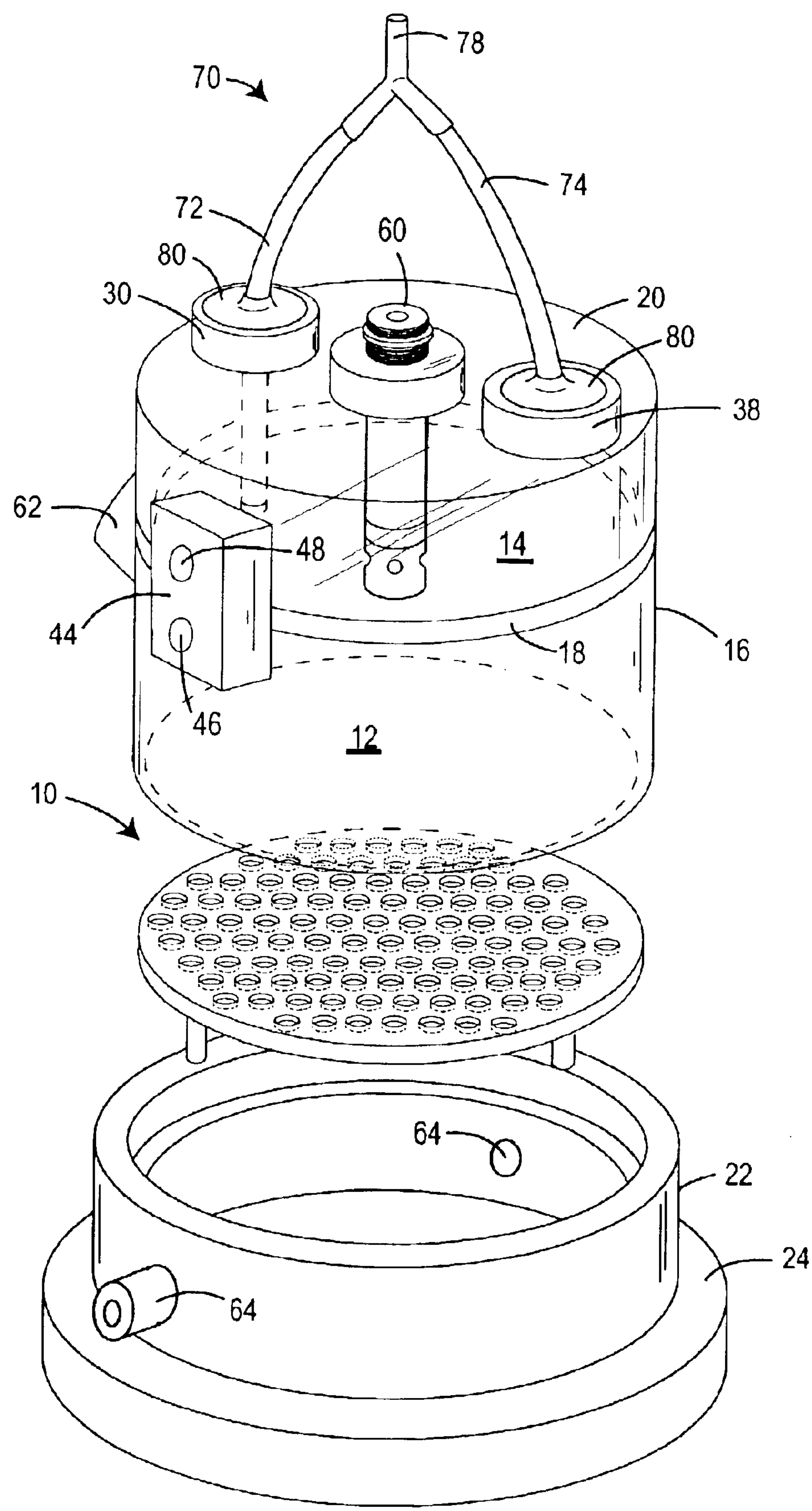
FIG. 1 is a perspective view of a preferred embodiment of the invention.
Figure 2:
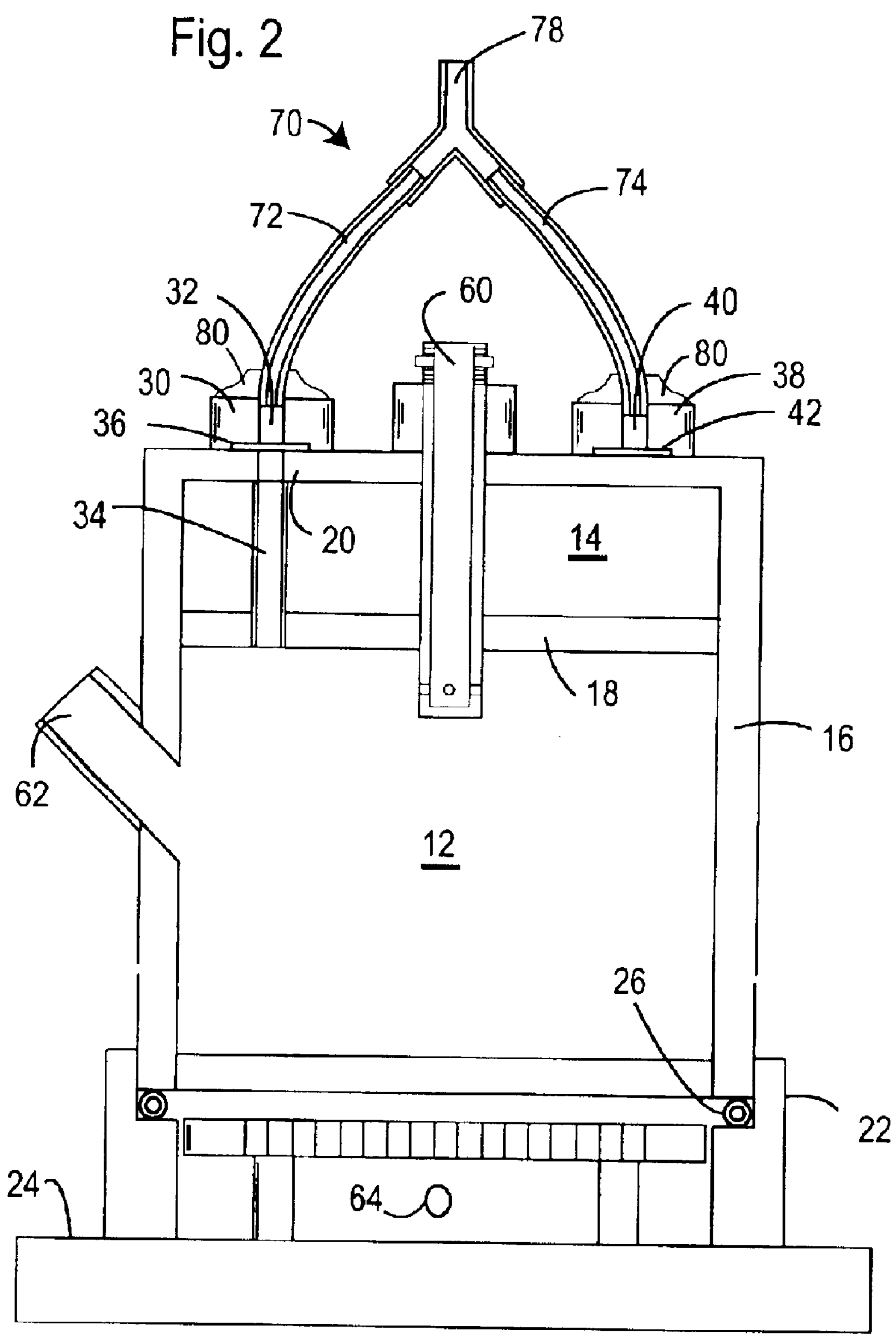
FIG. 2 is a sectional side view of the embodiment of FIG. 1.

FIGS. 1 and 2 illustrate a preferred embodiment of the invention comprised of a plethysmograph, generally 10, that includes a test chamber 12 and a reference chamber 14. Chambers 12 and 14 share a common cylindrical wall 16 that is divided into the two chambers by a common separator wall 18. A top wall 20 covers reference chamber 14. The lower end of common wall 16 is fitted into a cylindrical base wall 22, which rests on a footed base 24. An O-ring 26 around the exterior of wall 16 provides a seal between the walls 16 and base wall 22.

Test chamber pneumotach 30 mounted on top wall 20 includes an airflow inlet 32 in communication with a tube 34 that terminates within test chamber 12. A screen 36 is positioned between inlet 32 and tube 34 to provide a pressure drop for air flowing to or from test chamber 12. Similarly, a reference chamber pneumotach 38, also mounted on top wall 20, includes an airflow opening 40 opening into reference chamber 14, with screen 42 covering opening 40.

Figure 3:
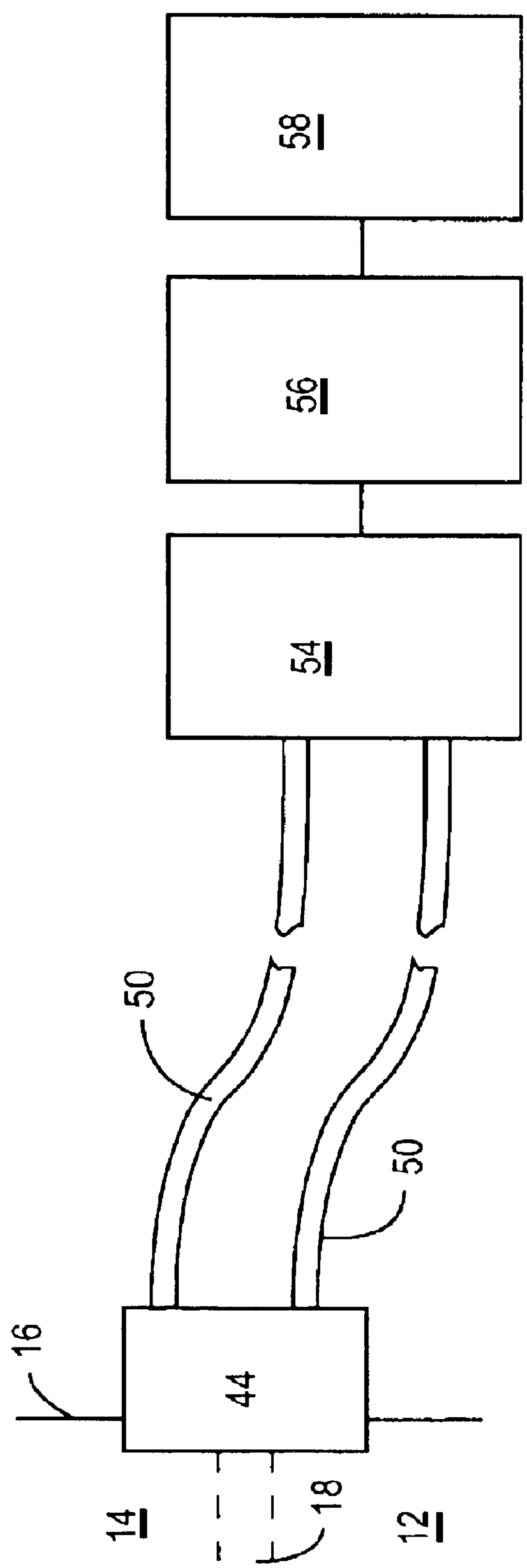
FIG. 3 is a schematic illustration of the plethysmograph transducer attached to a recorder through an amplifier.

Transducer block 44 is mounted on the outer surface of cylindrical wall 16 and spans separator wall 18. A first port 46 extends through block 44 to communicate with test chamber 12, while a second port 48 extends through block 44 to communicate with reference chamber 14. As illustrated schematically in FIG. 3, tubes 50 and 52 connect ports 46 and 48, respectively to differential pressure transducer 54 to measure pressure changes. Transducer 54 is connected through amplifier 56 to a recorder 58.

Plethysmograph 10 also includes an aerosol manifold 60 to introduce gases or aerosols into test chamber 12, a water bottle port 62, and bias-air exhaust port 64.

In order to further minimize measurement noise, plethysmograph 10 also includes a manifold, generally 70, having a split air passageway adapted to communicate with the airflow openings into pneumotachs 30 and 38 through tubes 72 and 74, respectively. Manifold 70 also includes an exterior airflow opening 78, with exterior air being drawn through opening 78 and then divided between tubes 74 and 76 to enter chambers 12 and 14. As a result, any fluctuations in air entering opening 78 will be communicated equally to both chambers, allowing subtraction of the resulting noise. As illustrated, tubes 72 and 74 are substantially of the same length so that any fluctuations enter the chambers at approximately the same time. Suction cups 80 secure the distal ends of tubes 72 and 74 to pneumotachs 30 and 38, respectively.

Figure 4:
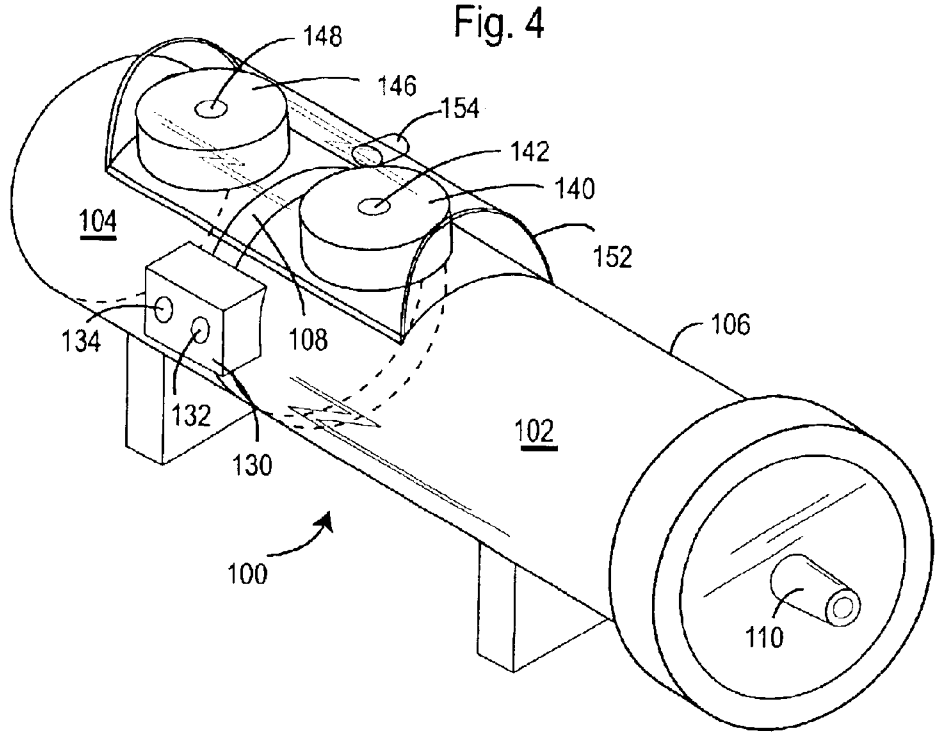
FIG. 4 is a perspective view of another embodiment of the invention.
Figure 5:
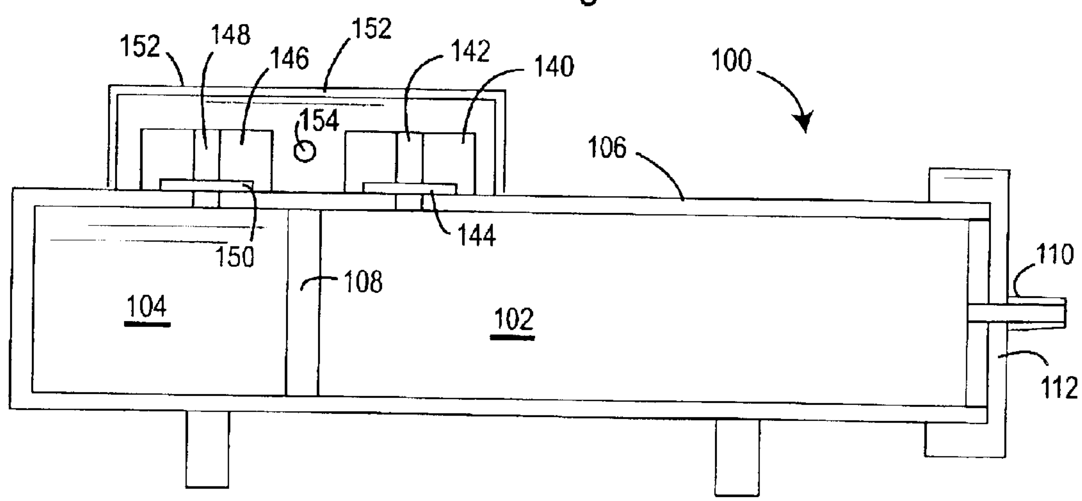
FIG. 5 is a sectional side view of the embodiment of FIG. 5.

FIGS. 4 and 5 illustrate a plethysmograph, generally 100, in which test chamber 102 and reference chamber 104 are horizontally oriented. As with the previously described plethysmograph, chambers 102 and 104 share a common cylindrical outer wall 106 and a common separator wall 108. An aerosol manifold 110 communicates with test chamber 102 through end wall 112.

Transducer block 130 is mounted on the outer surface of cylindrical wall 106 and spans separator wall 108. A first port 132 extends through block 130 to communicate with test chamber 102, while a second port 134 extends through block 130 to communicate with reference chamber 104.

Test chamber pneumotach 140 mounted on top of wall 106 includes an airflow opening 142 in communication with test chamber 102 through screen 144. Reference chamber pneumotach 146, mounted on top of wall 106 adjacent pneumotach 140 includes an airflow opening 148 in communication with reference chamber 104 through screen 150.

Pneumotachs 140 and 146 are covered with a common manifold housing 152 that includes an interior air passageway in communication with the openings of both pneumotachs. Housing 152 includes an exterior airflow opening 154. Exterior air is drawn through opening 154 into the passageway of housing 152, and from the passageway into the openings of pneumotachs 140 and 146. As a result, any fluctuations are communicated equally to both chambers. Further, the passage tends to create a non-turbulent zone that aids in minimizing turbulence.

Figure 6:
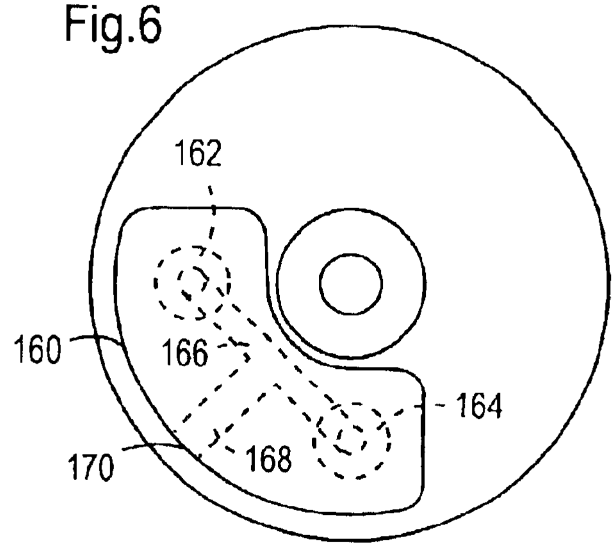
FIG. 6 is a top view of still another embodiment of the invention.
Figure 7:
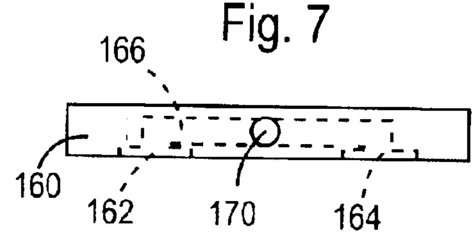
FIG. 7 is a side view of the manifold illustrated in FIG. 6.

FIGS. 6 and 7 illustrate a third embodiment, in which manifold, generally 160, is formed of a solid block of plastic or other material, drilled with pneumotach recesses 162 and 164, a first passageway 166 to communicate with the openings of pneumotachs inserted into recesses 162 and 164, and a second passageway 168 having an inner end in communication with passageway 166 equidistant between recesses 162 and 164, and an outer end forming an exterior airflow opening 170.

Figure 8:
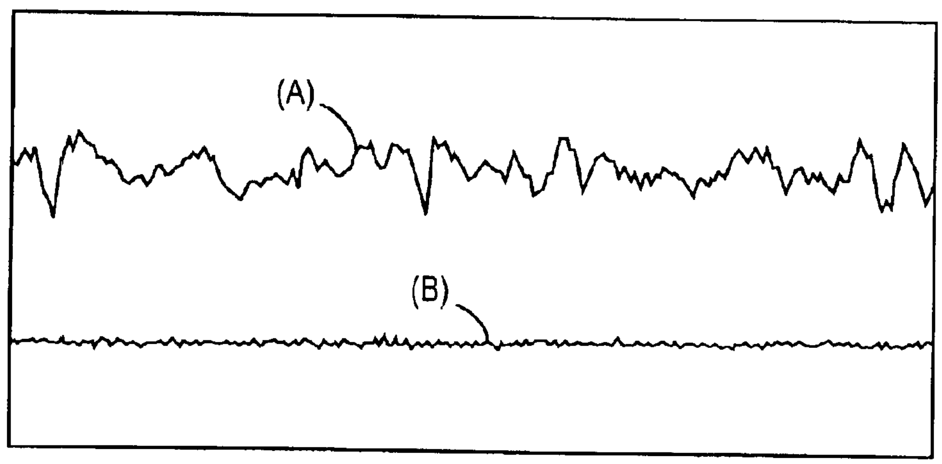
FIG. 8 is a graph of a tuned pneumotach illustrating the effect of dampening.

FIG. 8 graphically illustrates on a transducer voltage/time scale the dampening effect of the present invention, comparing noise from undampened pneumotachs (A) against dampened pneumotachs (B).

Certain modifications and improvements will occur to those skilled in the art upon a reading of the foregoing description. For example, the test and reference chambers may be positioned differently relative to each other and need not be separated by a common wall. The devices may also include other components common to plethysmographs. It should be understood that all such modifications and improvements have been deleted herein for the sake of conciseness and readability but are properly within the scope of the following claims.

What is claimed is:

1. A plethysmograph for transmitting reduced-noise pulmonary data from small animals to a differential pressure transducer comprising:

a) a test chamber for enclosing a small animal having a first pneumotach with an airflow opening and a first transducer port;

b) a reference chamber having a second pneumotach with an airflow opening and a second transducer port, said first and second transducer ports being adapted to communicate with said differential pressure transducer; and c) a manifold in communication with said first and second airflow openings, said manifold having an exterior airflow opening, and a passageway connecting said exterior airflow opening to said first and second airflow openings, whereby air entering both pneumotachs enters through said exterior airflow opening, thereby reducing noise in said transmitted data.

2. The plethysmograph of claim 1, wherein said manifold includes a housing covering said first and second airflow openings, said housing including an exterior airflow opening and a passageway between said exterior airflow opening and said first and second airflow openings.

3. The plethysmograph of claim 1, wherein said manifold includes a first passageway in communication with said first airflow opening, a second passageway in communication with said second airflow opening, said first and second passageways being in communication with a common exterior airflow opening.

4. The plethysmograph of claim 3, wherein said passageways are of substantially the same length.

5. The plethysmograph of claim 1, further including a first transducer outlet in communication with said test chamber and a second transducer outlet in communication with said reference chamber.

6. The plethysmograph of claim 1, further including a common wall separating said test chamber and said reference chamber.

7. The plethysmograph of claim 1, wherein said test chamber is cylindrical.

8. The plethysmograph of claim 1, further including an aerosol manifold in communication with said test chamber.

9. A plethysmograph for transmitting reduced-noise pulmonary data from small animals to a differential pressure transducer comprising:

a) a cylindrical outer wall;

b) a common separator wall dividing said cylindrical wall into a test chamber for enclosing a small animal and a reference chamber, said test and reference chambers having transducer ports adapted to communicate with said differential pressure transducer;

c) a first pneumotach having an airflow opening in communication with said test chamber;

d) a second pneumotach having an airflow opening in communication with said reference chamber; and e) a manifold in communication with the airflow openings of said first and second pneumotachs, said manifold having an exterior airflow opening, and a passageway connecting said exterior airflow opening to the openings of said pneumotachs, whereby air entering both pneumotachs enters through said exterior airflow opening, thereby reducing noise in said transmitted data.

10. The plethysmograph of claim 9, wherein said manifold includes a housing covering said pneumotachs, said housing including an exterior airflow opening and a passageway between said exterior airflow opening and the openings of said pneumotachs.

11. The plethysmograph of claim 9, wherein said manifold includes a first passageway in communication with the opening of said first pneumotach, a second passageway in communication with the opening of said second pneumotach, said first and second passageways being in communication with a common exterior airflow opening.

12. The plethysmograph of claim 11, wherein said tubes are of substantially the same length.

13. The plethysmograph of claim 9, further including a first transducer outlet in communication with said test chamber and a second transducer outlet in communication with said reference chamber.

14. A plethysmograph for transmitting reduced-noise pulmonary data from small animals to a differential pressure transducer comprising:

a) a vertical cylindrical outer wall;

b) a common separator wall dividing said cylindrical wall into a test chamber for enclosing a small animal and a reference chamber, said test and reference chambers having transducer ports adapted to communicate with said differential pressure transducer;

c) a top wall covering said cylindrical outer wall;

d) a first pneumotach mounted on said top wall in communication with said test chamber;

e) a second pneumotach mounted on said top wall in communication with said reference chamber; and f) a manifold having an exterior air inlet, a first passageway connecting said exterior air inlet to said first pneumotach, and a second passageway connecting said exterior air inlet to said second pneumotach, whereby air entering both pneumotachs enters through said exterior airflow opening, thereby reducing noise in said transmitted data.

15. The plethysmograph of claim 14, wherein said tubes are of substantially the same length.

16. The plethysmograph of claim 14, further including a first transducer outlet in communication with said test chamber and a second transducer outlet in communication with said reference chamber.

17. A plethysmograph for transmitting reduced-noise pulmonary data from small animals to a differential pressure transducer comprising:

a) a horizontal cylindrical outer wall;

b) a common separator wall dividing said cylindrical wall into a test chamber for enclosing a small animal and a reference chamber, said test and reference chambers having transducer ports adapted to communicate with said differential pressure transducer;

c) a first pneumotach mounted on said cylindrical wall in communication with said test chamber;

d) a second pneumotach mounted on said cylindrical wall in communication with said reference chamber; and e) a housing covering said first and second pneumotachs, said housing having an exterior air inlet, and a passageway connecting said exterior air inlet to said first and second pneumotachs, whereby air entering both pneumotachs enters through said exterior airflow opening, thereby reducing noise in said transmitted data.

18. The plethysmograph of claim 17, further including a first transducer outlet in communication with said test chamber and a second transducer outlet in communication with said reference chamber.

* * * * *